United States Patent [19]

Greene et al.

[11] Patent Number: 4,640,273
[45] Date of Patent: Feb. 3, 1987

[54] MOUTH GUARD FOR USE WITH A DIAGNOSTIC INSTRUMENT

[75] Inventors: Franklin R. Greene, Flushing; Howard S. Stern, Old Westbury; Jerome D. Waye, New York, all of N.Y.

[73] Assignee: E-Z-Em, Inc., Westbury, N.Y.

[21] Appl. No.: 731,882

[22] Filed: May 8, 1985

[51] Int. Cl.$^4$ .............................................. A61B 1/24
[52] U.S. Cl. ...................................... 128/136; 128/3; 128/207.14
[58] Field of Search ............. 128/136, 207.14, 200.26, 128/343, 303.11, 3, 4, 12, 303 R, 10, DIG. 26, 207.15, 207.16, 207.17

[56] References Cited

U.S. PATENT DOCUMENTS

| | | | |
|---|---|---|---|
| 1,498,810 | 6/1924 | Poe | 128/200.26 |
| 2,908,269 | 10/1959 | Cheng | 128/207.14 |
| 4,136,689 | 1/1979 | Shamlian | 128/207.14 |
| 4,152,017 | 5/1979 | Abramson | 128/207.14 |
| 4,166,467 | 9/1979 | Abramson | 128/207.14 |
| 4,270,529 | 6/1981 | Muto | 128/207.17 |
| 4,495,945 | 1/1985 | Liegner | 128/136 |
| 4,502,478 | 3/1985 | Lifton | 128/136 |

Primary Examiner—Henry J. Recla
Attorney, Agent, or Firm—McAulay, Fields, Fisher, Goldstein & Nissen

[57] ABSTRACT

This disclosure is directed to a disposable mouth guard constructed having a relatively hard, rigid core formed with an opening to permit passage therethrough of a diagnostic instrument, such as an endoscope. The core is sufficiently rigid to resist compression and prevent damage to the internal workings of the endoscope when the patient bites down on the center portion of the mouth guard. The outer surface of the core is provided with a relatively flexible soft coat to cushion the patient's bite.

11 Claims, 6 Drawing Figures

U.S. Patent  Feb. 3, 1987  4,640,273
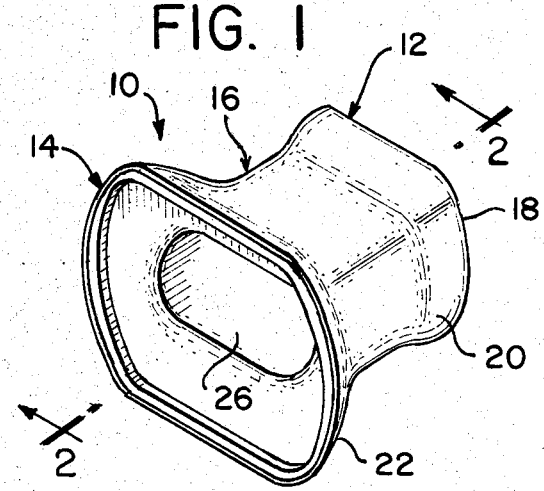
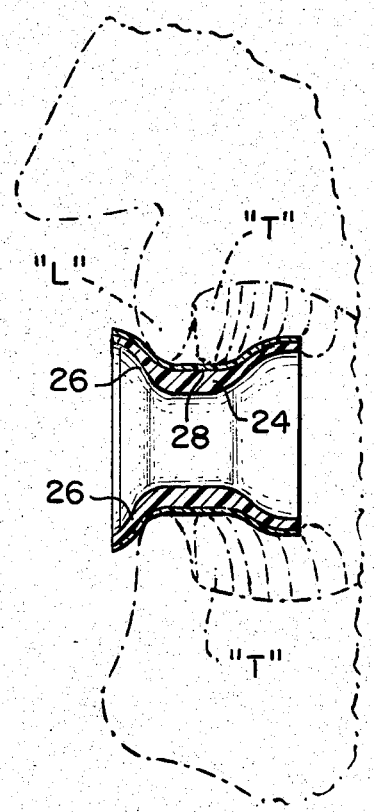
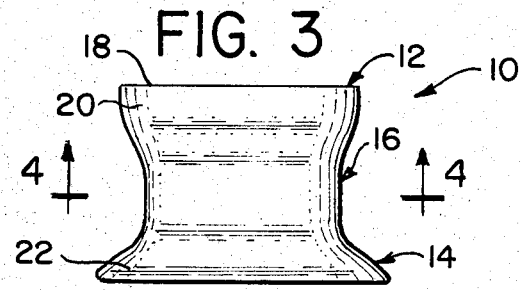
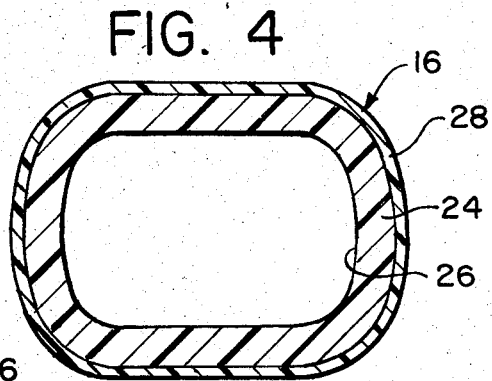
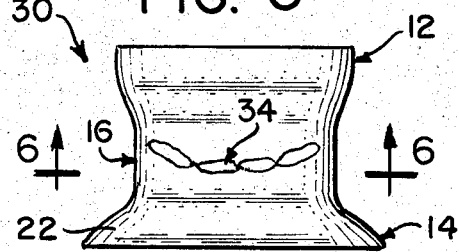
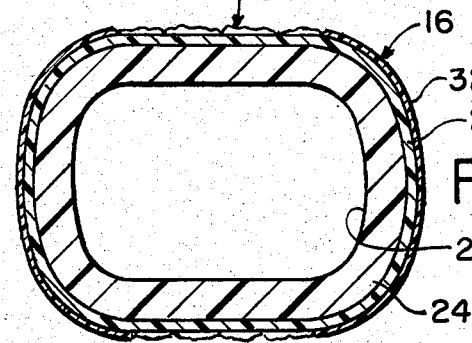

MOUTH GUARD FOR USE WITH A DIAGNOSTIC INSTRUMENT

BACKGROUND OF THE INVENTION

This invention is directed generally to mouth guards, and more specifically, to a disposable mouth guard for use with a diagnostic instrument, such as, an endoscope.

In the use of medical diagnostic instruments of the endoscope type, a mouth guard is first inserted into the patient's mouth and the barrel of the endoscope is then inserted through a central opening in the mouth guard. Without the presence of the mouth guard, the patient's reflex would tend to cause the patient's teeth to bite down on the barrel on the endoscope with the likelihood of causing damage to the internal components of the instrument such as, the light-transmitting optical fibers.

Since instruments of this kind are rather expensive, it is known to construct a mouth guard of substantially rigid plastic material which will resist compression. While such mouth guards achieve a desirable result in protecting the instrument, they have proven unsatisfactory in use. The primary disadvantage lies in the discomfort and possible injury to the patient when biting down on the hard material. On the other hand, if the mouth guard is made soft and high flexible, the added comfort to the patient in biting down will be off set by the increased likelihood of damage to the instrument.

The present invention provides a novel mouth guard which overcomes may of the disadvantages associated with the heretofore known rigid mouth guards. The mouth guard as hereinafter disclosed is relatively comfortable to the patient when in use while still affording protection to the delicate parts of the diagnostic instrument.

SUMMARY

The mouth guard of this invention has a first portion and a second portion connected together by a center portion. The first portion is adapted to be received within the patient's mouth. The second portion has an outwardly extending flange adapted to overlie the patient's lips when the first portion is in the patient's mouth. The center portion is adapted to be gripped by the patient when the mouth guard is in the patient's mouth.

The mouth guard has a relatively hard, rigid core formed with an opening to permit passage therethrough of the barrel of the endoscope. The core is sufficiently rigid to resist compression and prevent damage to the internal workings of the endoscope when the patient bites down on the center portion of the mouth guard. Although the core is hard and rigid, the outer surface of the core is provided with a relatively flexible, soft coat to cushion the patient's bite. The outer soft coat renders the mouth guard more comfortable when in use and lessens the likelihood of injury to the patient.

In another embodiment of the invention, the core is provided with a relatively thin second coat adapted to be ruptured by the patient's bite to expose the underlying first coat. This provides an indication that the mouth guard has already been used by a patient so that it will be discarded and not be inadvertently used again with another patient.

For a better understanding of the invention and its various features and advantages, reference should be made to the following detailed description when taken in conjunction with the accompanying drawings.

BRIEF DESCRIPTION OF THE DRAWINGS

FIG. 1 is a perspective view of a mouth guard embodying the present invention;

FIG. 2 is a cross-sectional view taken along line 2—2 of FIG. 1, with the mouth guard positioned in a patient's mouth represented by the phantom lines, and with the patient biting down on the center portion of the mouth guard;

FIG. 3 is top plan view of the mouth guard shown in FIG. 1;

FIG. 4 is a cross-sectional view taken along line 4—4 of FIG. 3;

FIG. 5 is a view similar to FIG. 3 showing another embodiment of the invention in which the core has a second coat deposited over the first coat, and in which the second coat has been ruptured by the patient's bite to expose the underlying coat; and FIG. 6 is a cross-sectional view taken along line 6—6 of FIG. 5.

DESCRIPTION OF THE PREFERRED EMBODIMENT

Referring to the drawings, there is shown a disposable mouth guard 10 constructed in accordance with the present invention. Mouth guard 10 has a first portion 12, a second portion 14, and a center portion 16 which serves to connect the first and second portions together.

First portion 12 extends radially outward from center portion 16, and has a relatively flexible edge 18 which defines a rounded outer surface 20. First portion 12 is adapted to be received within the patient's mouth when in use.

The second portion 14 of mouth guard 10 has an outwardly extending flange 22. When the mouth guard is positioned in the patient's mouth, as shown in FIG. 2, the flange 22 is deposited to overlie the patient's lips "L". The flange serves to center the mouth guard in place, and effectively prevents the mouth guard from being fully inserted or drawn into the patient's mouth when in use. FIG. 2 also shows the center portion 16 being gripped by the patient's teeth "T" when the mouth guard 10 is in the patient's mouth.

In construction, mouth guard 10 includes a rigid core 24 formed having an opening 26 which serves as a passageway through which passes the barrel of an endoscope in conventional manner. The surface of core opening 26 is smooth and slippery to facilitate insertion of the endoscope. Core 24 is sufficiently rigid to resist compression and prevent damage to the working components of the inserted endoscope, including the light-transmitting optical fibers, when the patient bites down on the center portion 16 of mouth guard 10.

In accordance with the teaching of the invention, the outer surface of core 24 is provided with a relatively flexible, soft coat 28 to cushion the patient's bite. The surface of the outer soft coat 28 is smooth and non-slippery. Coat 28 renders the mouth guard more comfortable when in use and lessens the likelihood of injury to the patient.

In manufacture, the mouth guard is made of plastisol by a dip molding process, and has the shape of an annular oval. However, the core 24 and the coat 28 are of different plasticized materials. Specifically, whereas the core 24 has very little plasticizer, the coat 28 is highly plasticized. Aside from the different plasticized materials, which require separate dipping and curing steps, the dip molding technique is conventional and well known in the art. The thickness of core 24 is approximately 0.125". The thickness of coat 28 is approximately between 0.010" and 0.020".

FIGS. 5 and 6 show another embodiment of the invention, represented by mouth guard 30, wherein core 24 is provided with a relatively thin second coat 32. Aside from this second coat, the construction of mouth guards 10 and 30 is the same. Coat 32 also is applied by a dip molding process, and has a thickness approximately between 0.002" and 0.003". Coat 32 is intended to be ruptured by the patient's bite in the region represented generally by numeral 34 to expose the underlying first coat 28.

It is intended that coat 28 and coat 32 will be of different colors, Thus, when selecting a mouth guard for use, if the color of the underlying coat 28 is exposed to view through the ruptured portion 34 of coat 32, the doctor or technician will immediately know that the mouth guard had been previously used and will be discarded. This reduces the likelihood of the mouth guard being inadvertently used again with another patient. If desirable, the coats 28 and 32 could be flavored to present a pleasant taste when the patient bites down on the mouth guard.

It is further intended that the mouth guard can be manufactured and sold sufficiently cheaply in a sterile condition to make it economically worthwhile to be used once and discarded.

While the present invention has been described with respect to particular embodiments, it will be readily appreciated and understood that numerous variations and modifications thereof may be made without departing from the spirit or scope of the claimed invention.

We claim:

1. An annular disposable mouth guard having a main axis, said mouth guard comprising:
    a relatively rigid center annular portion adapted to be held by a patient's teeth,
    a first annular end portion, said first portion extending axially inward and radially outward from said center portion and adapted to be received within a patient's mouth;
    a second annular end portion, said second portion extending axially forward and radially outward from said center portion to form a flange adapted to overlie the patient's lips when said first portion is in the patient's mouth;
    a relatively hard plastic core extending through said first, center and second portions, said core having an opening to permit passage of a diagnostic instrument therethrough, said core being sufficiently rigid at said center portion to resist compression and prevent damage to the inserted diagnostic instrument when the patient bites down on said center portion of said mouth guard; and
    a relatively soft plastic coat formed on the radially outer surface of said core to cushion the patient's bite,
    the plastic material of said core being sufficiently flexible to provide a relatively flexible edge at the axially inward end of said first portion.

2. The mouth guard of claim 1, wherein said inner end of said first portion has a rounded surface.

3. The mouth guard of claim 1, wherein the surface of said core opening is smooth and slippery, and the surface of said coat is smooth and non-slippery.

4. The mouth guard of claim 1, wherein said core has a thickness of approximately 0.125" and said coat has a thickness of approximately between 0.010"-0.020".

5. The mouth guard of claim 1, wherein said core has a second coat formed on said first coat, said second coat having a color contrasting with the color of said underlying first coat, and said second coat adapted to be ruptured by the patient's bite to expose said first coat.

6. The mouth guard of claim 5, wherein said second coat has a thickness approximately between 0.002"-0.003".

7. The mouth guard of claim 1, wherein the outer surface of said mouth guard is an annular oval.

8. An annular disposable mouth guard having a main axis for use with a diagnostic instrument, said mouth guard comprising:
    a relatively rigid center annular portion adapted to be held by a patient's teeth,
    a first annular end portion, said first portion extending axially inward and radially outward from said center portion and adapted to be received within a patient's mouth;
    a second annular end portion, said second portion extending axially forward and radially outward from said center portion to form a flange adapted to overlie the patient's lips when said first portion is in the patient's mouth;
    a relatively hard plastic core extending through said first, center and second portions, said core having an opening to permit passage of the diagnostic instrument therethrough, said core being sufficiently rigid at said center portion to resist compression and prevent damage to the inserted diagnostic instrument when the patient bites down on said center portion of said mouth guard;
    a relatively soft plastic coat formed on the radially outer surface of said core to cushion the patient's bite, and
    a second plastic coat formed on said first coat, said second coat having a color contrasting with the color of said underlying first coat, said second coat adapted to be ruptured by the patient's bite to expose said first coat;
    the plastic material of said core being sufficiently flexible to provide a relatively flexible edge at the axially inward end of said first portion.

9. The mouth guard of claim 8, wherein said inner end of said first portion has a rounded surface.

10. The mouth guard of claim 8, wherein the surface of said core opening is smooth and slippery, and the surface of said second coat is smooth and non-slippery.

11. The mouth guard of claim 8, wherein the outer surface of said mouth guard is an annular oval.

* * * * *